(12) United States Patent  (10) Patent No.: US 7,541,178 B2
Takagi et al.  (45) Date of Patent: Jun. 2, 2009

(54) CELL/TISSUE CULTURE APPARATUS

(75) Inventors: Takao Takagi, Fuji (JP); Setsuo Watanabe, Fuji (JP)

(73) Assignee: Takagi Industrial Co., Ltd., Shizuoka-ken (JP)

( * ) Notice: Subject to any disclaimer, the term of this patent is extended or adjusted under 35 U.S.C. 154(b) by 746 days.

(21) Appl. No.: 10/497,515

(22) PCT Filed: Nov. 19, 2002

(86) PCT No.: PCT/JP02/12083

§ 371 (c)(1),
(2), (4) Date: Jun. 3, 2004

(87) PCT Pub. No.: WO03/048296

PCT Pub. Date: Jun. 12, 2003

(65) Prior Publication Data

US 2005/0048643 A1  Mar. 3, 2005

(30) Foreign Application Priority Data

Dec. 5, 2001  (JP) ............................. 2001-371966

(51) Int. Cl.
C12M 3/00  (2006.01)

(52) U.S. Cl. .............. 435/289.1; 435/293.1; 435/299.1; 366/275; 623/915

(58) Field of Classification Search .............. 435/304.1, 435/304.2, 305.2; 623/7, 8, 23.64, 915; 366/275; 604/408

See application file for complete search history.

(56) References Cited

U.S. PATENT DOCUMENTS 5,261,255 A * 11/1993 Coelho et al. .................. 62/376
5,426,037 A *  6/1995 Pannell et al. ............. 435/70.21
6,121,042 A     9/2000 Peterson et al.

FOREIGN PATENT DOCUMENTS

| EP | 0586922 A1 | 3/1994 |
| FR | 2 799 138 A1 | 4/2001 |
| JP | 620501119 A | 5/1987 |
| JP | 6-181750 A | 7/1994 |
| JP | 7-8260 A | 1/1995 |

(Continued)

OTHER PUBLICATIONS

Supplementary European Search Report issued in corresponding European Patent Application No. 02804350.3 on Aug. 13, 2007.
International Search Report PCT/JP01/12083, Jan. 14, 2003.

*Primary Examiner*—William H Beisner
(74) *Attorney, Agent, or Firm*—Connolly Bove Lodge & Hutz LLP

(57) ABSTRACT

A cell/tissue culture apparatus is suitable for a culture of a cultivated object of a cell or tissue adapted for a prescribed portion of a living body of a breast and so on, a culture chamber (18, a culture vessel 10) which accommodates a cell or tissue to be cultivated and also makes a culture fluid (34) circulate is formed by a flexible material (flexible films 12, 14), and the culture chamber is immersed in a fluid (water 8). A pressure or an oscillation is given to the culture chamber installed in the fluid, and a physical stimulation due to the pressure from the fluid or the oscillation of the fluid is given to a cell or tissue under a culture.

9 Claims, 8 Drawing Sheets

FOREIGN PATENT DOCUMENTS

| | | | |
|---|---|---|---|
| JP | 09206069 A * | 8/1997 | |
| JP | 2002-500004 A | 1/2002 | |
| WO | WO 86/02664 | 5/1986 | |
| WO | WO 9813469 A1 * | 4/1998 | |
| WO | WO-98/30676 A | 7/1998 | |
| WO | WO 99/33951 | 7/1999 | |

* cited by examiner

CELL/TISSUE CULTURE APPARATUS

TECHNICAL FIELD

The present invention relates to a cell/tissue culture apparatus used for a culture of a cell or tissue, and so on, to which tissue engineering is applied. More particularly, the present invention relates to a cell/tissue culture apparatus for efficiently realizing a metabolism function of a cell or tissue when performing an in vitro culture of a cell or tissue of a living body of a human body and so on, and for giving a physical stimulation necessary for prolongation, differentiation and promotion of a cell to an cultivated object.

BACKGROUND ART

In a conventional method which performs an in vitro culture of a cell or tissue of a living body of a human body and so on, there is employed a method in which temperature, humidity, the concentration of carbon dioxide and the concentration of oxygen in an incubator (a culture house) are maintained at proper conditions, and a cell is cultivated in that incubator. A cell or tissue is placed in a culture fluid in a floating state, or a cell or tissue is fixed to an inside or a surface of a gel in which an ingredient of the culture fluid is input, and thereby, the cell or tissue is made to proliferate and to grow. Or, a cell or tissue is transplanted in a material, which is called a matrix or a scaffold, a carrier or a mold, and so on (herein after called "matrix" simply), and thereby, the cell or tissue is made to proliferate and to grow.

In this case, for the proliferation and growth of the cell or tissue, it is important to give a physical stimulation to the cell or tissue to be cultivated in addition to environmental conditions of temperature, humidity, the concentration of carbon dioxide, the concentration of oxygen, and so on. Such a physical stimulation is an indispensable factor for promoting differentiation and growth of a cell or tissue and for growing to a cell or tissue closer to a cell or tissue in a living body. As a technology which gives a physical stimulation to the proliferation and growth of a cell or tissue, there are, for example, the Japanese Official Announcement Patent Publication No. 2001-504697 entitled "APPLICATION OF SHEAR FLOW STRESS TO CHONDROCYTES" and the Japanese Patent No. 3163533 entitled "LOADING DEVICE OF EXPANDING AND CONTRACTING STIMULATION FOR CULTURING CELL BY USING SILICON BELT".

By the way, as for a restoring method of a breast to a patient whom an eliminating operation of the breast has been performed owing to breast cancer and soon, a method which injects silicone into an excised portion, and so on are general. The silicone as a material for restoring a shape is much used as a material adapted to a living body, which is non-absorbability toward a living body. However, if it is maintained for a long term in a living body, there is indication that an outflow of the silicone into the living body can not be avoided, and so on. Because of this, without using a foreign substance of the silicone and so on, restoration of a deficient portion by means of a tissue similar to a living body is strongly desired.

The present invention, therefore, makes it an object to provide a cell/tissue culture apparatus suitable for a culture of a cultivated object of a cell or tissue which is adapted to a prescribed portion of a living body of a breast and so on.

DISCLOSURE OF THE INVENTION

A cell/tissue culture apparatus of the present invention makes it a feature to form a culture chamber (18, a culture vessel 10), which accommodates a cell or tissue to be cultivated and also makes a culture fluid (34) circulate, by a flexible material (flexible films 12, 14), and to immerse this culture chamber in a fluid (water 8). If the cell or tissue to be cultivated is housed in the culture chamber formed by the flexible material, if the culture fluid is made to circulate, and, along with these, if the culture chamber is made to immerse in the fluid, it is possible to apply a pressure from the fluid to an inside of the culture chamber from an outside of the culture chamber, and this pressure becomes a physical stimulation toward the cell or tissue to be cultivated. Therefore, it is possible to cultivate a tissue body according to a shape of a desired portion in a human body, and it is also possible to realize flexibility and toughness which the portion has.

In the cell/tissue culture apparatus of the present invention, the apparatus makes it a feature to give a physical stimulation to said cell or tissue in said culture camber by making said fluid oscillate. If the cell or tissue to be cultivated is accommodated in the culture chamber formed by flexible material, if the culture fluid is made to circulate, if the culture chamber is made to immerse in the fluid, and, along with these, if a pressure and/or a vibration is applied to an inside of the culture chamber with the fluid used as a medium from an outside of the culture chamber, an oscillation of the fluid is applied to the cell or tissue in the culture chamber as a physical stimulation.

In the cell/tissue culture apparatus of the present invention, said culture chamber makes it a feature to provide a space part of a shape according to a shape of cells or tissue to be cultivated. That is, in a cell or tissue to be cultivated, for example, there are cases in which it is rendered necessary to cultivate in a shape of a portion of a human body to be restored. Because of this, if the space part of the culture chamber corresponds with a shape of said portion, it is possible to make the culture chamber function as a mold for formation, and it is possible to cultivate/produce a tissue body corresponding to the shape of a desired portion.

In the cell/tissue culture apparatus of the present invention, said oscillation of the fluid makes it a feature to be due to a jet of fluid. That is, the jet of fluid can generate an optional oscillation in the fluid. If this jet is applied through the fluid to the culture chamber, it is possible to give a physical stimulation of pressure, vibration and soon according to modes of strength and so on of the jet to a cell or tissue to be cultivated. This physical stimulation can be controlled according to modes of strength, direction and so on of the jet.

In the cell/tissue culture apparatus of the present invention, said oscillation of the fluid makes it a feature to be due to wave motion. That is, there are a transverse wave and a longitudinal wave in the wave motion, and the wave motion has variational factors of a period, a level and so on. Hence, if an oscillation is generated in the fluid by this wave motion, control of the oscillation is easy by means of an adjustment of the wave motion, and it is possible to generate wave motion which is desired. As a result, it is possible to give a physical stimulation, which is desired, to a cell or tissue.

In the cell/tissue culture apparatus of the present invention, said physical stimulation makes it a feature to be a shearing stress. By giving the shearing stress to a cell or tissue, a tough tissue can be obtained.

In the cell/tissue culture apparatus of the present invention, said physical stimulation makes it a feature to be given intermittently or continuously. In order to cultivate a tissue equivalent to a human body, by making intermittence or continuousness of the physical stimulation, it is possible to give a stimulation equivalent to a human body to a cell or tissue.

And, the objects, features, advantages and so on of the present invention will be more clear by referring to an explanation in the modes for carrying out the present invention and embodiments shown in the drawings.

BEST MODES FOR CARRYING OUT THE INVENTION

Figure 1:
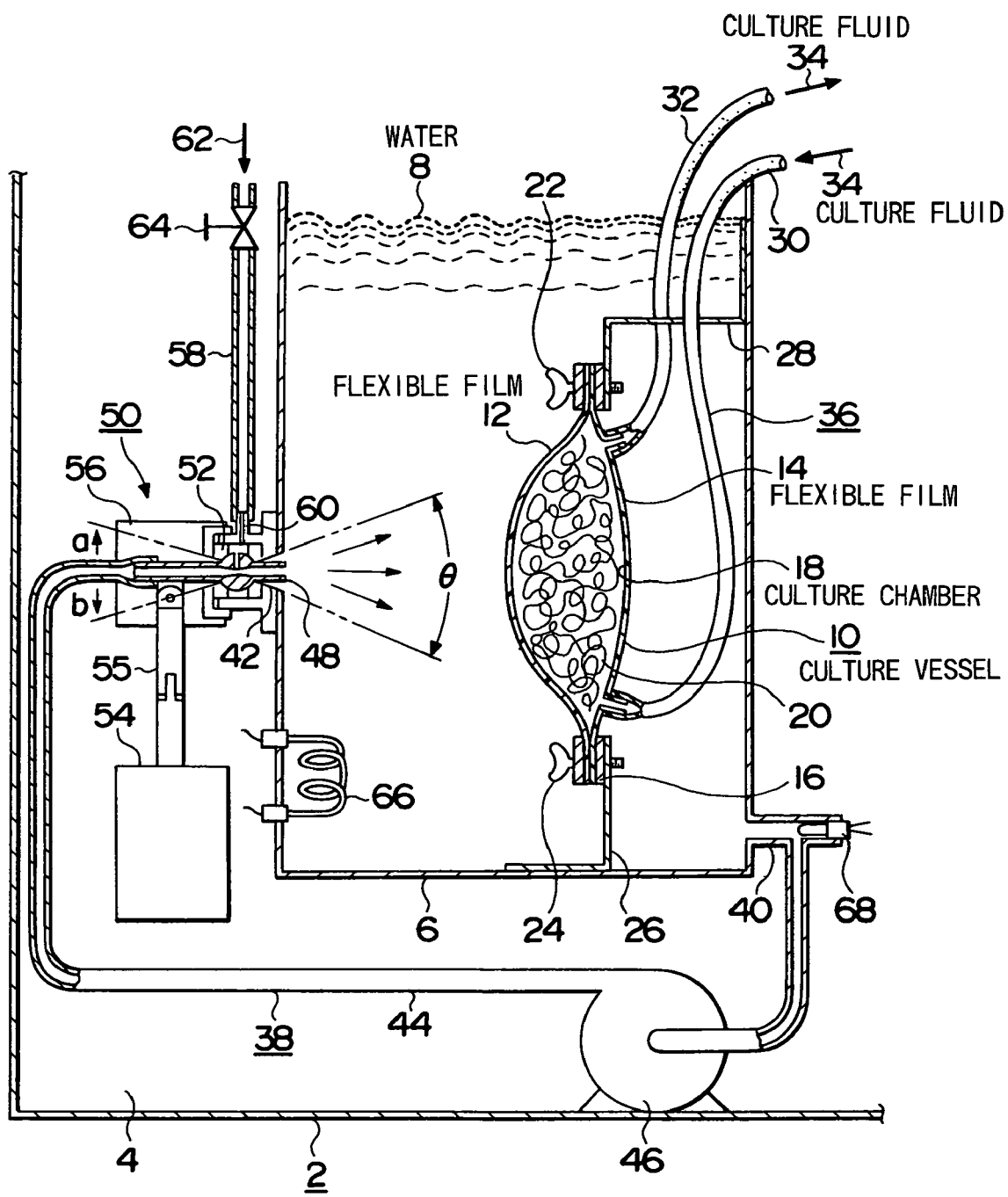
FIG. 1 is a drawing showing a first embodiment of a cell/tissue culture apparatus according to the present invention.

In the following, modes for carrying out the present invention are explained by referring to embodiments shown in the drawings.

Figure 2:
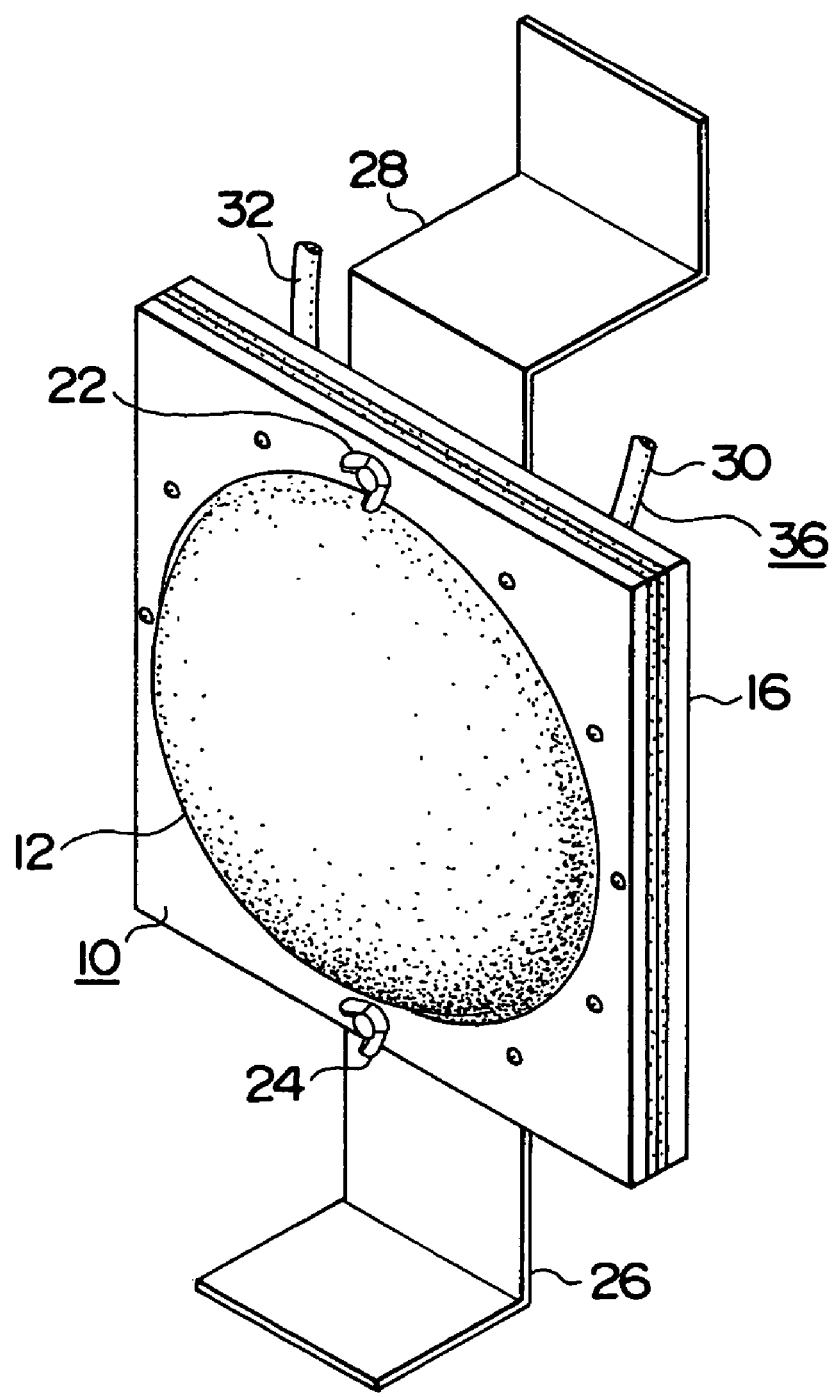
FIG. 2 is a perspective view showing a culture unit.
Figure 3:
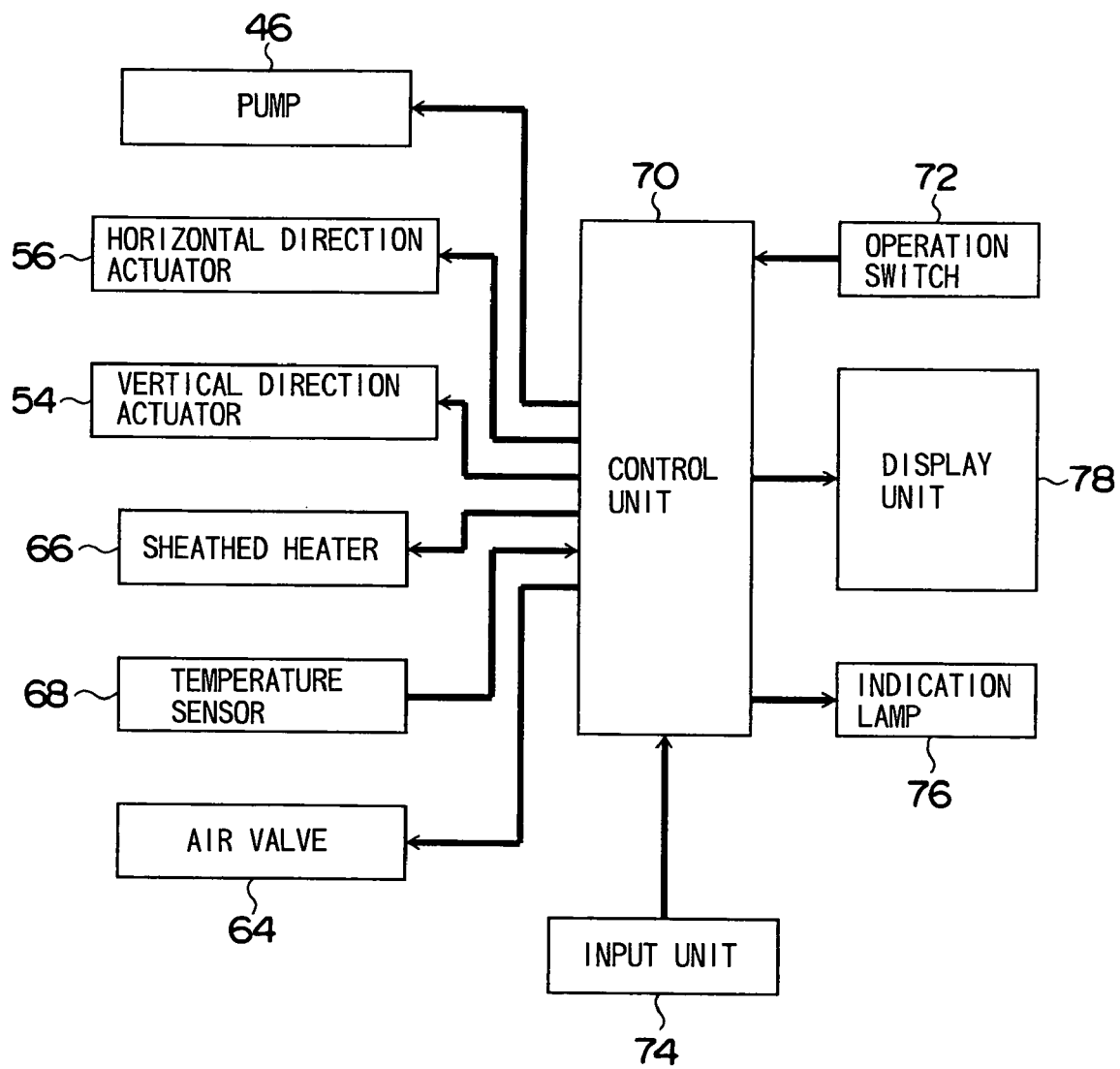
FIG. 3 is a block diagram showing an embodiment of a culture control device.

FIG. 1 through FIG. 3 show a first embodiment of a cell/tissue culture apparatus according to the present invention. FIG. 1 shows a whole configuration of the cell/tissue culture apparatus, FIG. 2 shows a culture unit, and FIG. 3 shows a culture control device.

To this cell/tissue culture apparatus, an apparatus body 2 is provided. This apparatus body 2 is a means which forms an aseptic space 4 suitable for a culture. A culture bath 6 is installed in an inside of this apparatus body 2, and, as a fluid, for example, water 8 is stored in the culture bath 6. Instead of this water 8, oil and so on having proper viscosity may also be used. This culture bath 6 which stores up the water 8 may be any shape of a circular cylindrical body, a square cylindrical body, and so on. It is desirable that the culture bath 6 is formed by a corrosion-resistant material of stainless steel and so on.

In an inside of this culture bath 6, as a culture vessel which cultivates a cell or tissue, for example, a culture vessel 10 shown in FIG. 2 is installed. This culture vessel 10 is immersed in an interior of the water 8, and receives a pressure namely a water pressure, which is a physical stimulation, according to a depth at which the culture vessel 10 is immersed. The culture vessel 10 is a thing that flexible films 12 and 14 which are a pressure reception member and a forming member formed by a flexible material of rubber and so on are attached to a frame member 16. And a culture chamber 18 of a predetermined shape is formed by each of the flexible films 12 and 14. Each of the flexible films 12 and 14 has properties that a heat resistance is high and that gas and liquid are difficult to penetrate, and has a chemically stable characteristic that an outflow of an ingredient by dissolution is very little. The flexible films 12 and 14 are formed by a synthetic resin safe and stable for a living body, for example, by a film made of fluororesin. As a culture medium which becomes a scaffold of the cell or tissue, for example, a matrix 20 consisting of a bioabsorbable material is accommodated in the culture chamber 18. The matrix 20, for example, is a thing that a bioabsorbable material of a long thread-shape is rounded so as to be tangle into one at random. Its shape is a shape similar to a breast of a patient, and it is a thing that reproduces a shape before an operation.

In case of this embodiment, the culture vessel 10 is fixed in the inside of the culture bath 6 by attaching the frame member 16, which maintains the flexible films 12 and 14, to support members 26 and 28 by thumbscrews 22 and 24 which are a fixing means. One support member 26 is protrusively provided at a side of a bottom face of the culture bath 6, and the other support member 28 is protrusively provided at a side of an inner side wall of the culture bath 6. By this, the culture chamber 18 of the culture vessel 10 which consists of the flexible films 12 and 14 is set at a predetermined position in the culture bath 6.

Further, to the culture vessel 10, two tubes 30 and 32 are attached at a side of the flexible film 14, and a circulation path 36 of a culture fluid 34 is formed by these tubes 30 and 32. Therefore, for the matrix 20 which is set to the inside of the culture vessel 10, the culture fluid 34 necessary for a culture is circulated and is supplied.

Further, to the culture bath 6, a means which generates oscillation and/or variation in the water 8 as a fluid is provided. In this embodiment, a jet generation mechanism 38 is installed. The jet generation mechanism 38 is a thing that pressure-feeds the water 8, which is taken out of the culture bath 6 to an outside, to the inside of the culture bath 6 to hit on the culture vessel 10, and also generates an oscillation for the water 8 in the culture bath 6.

In case of this embodiment, to the culture bath 6, a taking-out opening 40 of the water 8 is provided at a side of its bottom face, and a return opening 42 is formed at a side wall portion of a face side opposite to the taking-out opening 40. Further, a circulation path 44 which makes the water 8 circulate is formed between the taking-out opening 40 and the return opening 42, and a pump 46 serving as a pressure-feed circulation means of the water 8 is installed in the circulation path 44. It is possible to optionally adjust the strength of a pressure-feed flow by a rotation of the pump 46.

Further, a nozzle 48 serving as a jet injection means which injects the water 8 pressure-fed through the circulation path 44 is provided at a side of the return opening 42. In order to vary a jet generated from the nozzle 48 in vertical and horizontal directions, the nozzle 48 is attached to a vertical/horizontal operation mechanism 50. In the embodiment, a vertical direction actuator 54 serving as a vertical direction turning means which turns the nozzle 48 in a vertical direction with a venturi part 52 provided at an intermediate portion of the nozzle 48 and used as a supporting point is provided, and a horizontal direction actuator 56 serving as a horizontal direction turning means which turns the nozzle 48 in a horizontal direction is provided. For example, a plunger 55 of the vertical direction actuator 54 is pivoted at a rear portion of the nozzle 48. In addition, a mechanism turning the nozzle 48, for example, can be constituted so that an external shape of the venturi part 52 is formed into a ball part, so that this ball part is snapped by a rotatable support member consisting of a synthetic resin and is supported in a rotatable state by the support member, and so that moving force in a vertical direction or a horizontal direction is given to an intermediate portion of the nozzle 48 by using this as a supporting point.

To the vertical direction actuator 54 and the horizontal direction actuator 56, a motor is provided as a drive means, respectively. The actuators 54 and 56 convert a rotation of each motor into a movement of a vertical direction or a horizontal direction, and can move the nozzle 48 in the vertical direction or the horizontal direction, or in the vertical and horizontal directions at the same time. That is, by turning in every direction, a directional movement over a solid angle 90° is possible, and it is possible to uniformly inject a jet on the culture vessel 10.

Further, a means which adds a bubble flow to a jet is provided to the nozzle 48, and, in this embodiment, an air intake tube 58 is connected to the venturi part 52 of the nozzle 48. For example, a throat 60 is formed at the venturi part 52 of an intermediate portion of the nozzle 48, and the air intake tube 58 is joined to a small hole for an air intake which is formed at a constricted portion of the throat 60. An opening end of the air intake tube 58 is installed at a position slightly higher than the surface of water in the culture bath 6. Further, an air valve 64 which adjusts an intake of air 62 is provided to the air intake tube 58, and existence or non-existence of a bubble flow and its amount can be adjusted by the air valve 64. The air 62 which is drawn from the air intake tube 58 by a pressure-feed of a water flow makes a bubble flow occur in the water 8, and it is possible to generate ultrasonic waves in the water 8 by the bubble flow.

Further, to the inside of the culture bath 6, a sheathed heater 66 serving as a heating means which keeps the water 8 warm is attached. In addition, to the taking-out opening 40 of the water 8, a temperature sensor 68 serving as a water temperature detection means of the inside of the culture bath 6 is attached.

A detection output of the temperature sensor 68, as shown in FIG. 3, is given to a control unit 70 which is provided as a culture control means. The control unit 70 has a processor, a storage means, an input-output means, and so on. For the control unit 70, an operation switch 72 which orders operation of the apparatus and a stop of the operation, and an input unit 74 serving as a means which sets a stimulation mode and so on and takes in various kinds of control outputs are provided. Further, an indication lamp 76 which performs indication of a state of operation or a stop state of the operation, and a display unit 78 serving as a display means which displays a state of affairs in a culture, and so on are provided. In addition, this control unit 70 generates various kinds of control outputs, and gives each control output to the pump 46, each of the actuators 54 and 56, the heater 66 or the air valve 64.

In a composition like this, the matrix 20 of a bioabsorbable material which makes a scaffold for a culture of a cell or tissue is put in the inside of the culture chamber 18, and an adipose cell is planted in the matrix 20. Because of the culture and the growth of a nerve, it is better to fix also NGF (Nerve Growth Factor) to the scaffold at the same time. The culture chamber 18 in which such a matrix 20 is accommodated, namely the culture vessel 10, is immersed in the water 8 of the culture bath 6.

In the culture chamber 18, the culture fluid 34 is circulated. Along with this, the water 8 in the culture bath 6 is circulated through the circulation path 44 by the pump 46, and is injected into the culture bath 6 by the nozzle 48. A water temperature in the culture bath 6 is detected by the temperature sensor 68, a heating temperature of the sheathed heater 66 is adjusted according to the detected temperature, and the water temperature is controlled to a certain temperature.

If the pump 46 is operated, the water 8 is circulated through the circulation path 44. Along with this, a jet is generated from the nozzle 48, and the jet is hit on the culture chamber 18. A direction of the jet can be varied by driving the two actuators 54 and 56, and it is possible to give the jet to an optional position of a surface of the culture chamber 18. In the culture chamber 18 with which the jet collides, that collision part is pressed, and deformation is also caused at its circumferential part. If an injecting direction of the jet is varied, shearing stresses of all directions are applied to the cell or tissue on the matrix 20 of the culture chamber 18, in other wards, a massage force is applied. For example, if the rear side of the nozzle 48 is moved in the directions of an arrow "a" or "b" by the actuator 54, a pointed end side of the nozzle 48 moves in a vertical direction with the venturi part 52 used as a supporting point, and is to be swung in the range of an angle θ according to magnitude of move displacement which is applied. Operation like this is also performed by the actuator 56, and the nozzle 48 is to be swung in an angle range by a horizontal direction movement.

Further, if the air valve 64 is opened, since the venturi part 52 is under a state of a negative pressure due to the occurrence of a jet by the pump 46, the air 62 is sucked into the jet. By this, the air 62 becomes minute bubbles, mixes with the jet, and is injected into the water 8 of the culture bath 6 from the nozzle 48. The minute bubbles generate ultrasonic waves, give a vibrational stimulation to the cell or tissue on the matrix 20, and produce a good effect.

Like this, an optimum pressure is maintained by a pressure by-pass valve not shown in the drawings while a shearing stress due to a jet of the water 8 is being given to a cell or tissue on the matrix 20, and, under this state, it is possible to make the culture fluid 34 circulate in the culture chamber 18 and to cultivate the cell or tissue. Further, by varying the velocity of a jet by control of a rotating speed of the pump 46, and so on, it is possible to give an optimum physical stimulation to the cell or tissue on the matrix 20. In this case, strength of the jet given to the cell or tissue, for example, is controlled by a program which varies a rotating speed of the pump 46 so as to make an optimum stress with the lapse of a culture time. Further, by adjustment of an amount or water level of the water 8, it is also possible to adjust a hydrostatic pressure given to a culture part. As a result, it is possible to give physical stimulation of two kinds of the hydrostatic pressure and the shearing stress.

In this embodiment, the culture vessel 10 is fixed to the culture bath 6. However, a composition able to vary a depth of immersion to the water 8 can be given, and, if the magnitude of a water pressure applied to the culture vessel 10 namely the culture chamber 18 is varied, it is possible to give an optimum physical stimulation due to variation in a water pressure to the cell or tissue on the matrix 20. Further, in case in which the culture vessel 10 is fixed to the culture bath 6, by varying an amount of the water 8, likewise it is possible to give a physical stimulation due to a water pressure. Furthermore, by using a sterilizing fluid for the water 8 in the culture bath 6, and by performing the improvement of bacteria-proof of the aseptic space 4 and the culture bath 6, it is possible to give higher contamination control of the prevention of admission of bacteria to the culture chamber 18, and so on.

Furthermore, according to this cell/tissue culture apparatus, it is possible to give a shearing stress to the whole of a tissue under a culture from a random direction. That is, by giving the shearing stress to the whole of the tissue from a random direction, in other words, by giving a massage force, it is possible to cultivate a tissue with a lot of gapes, namely, a tender adipose tissue. In the adipose tissue having a lot of gapes, flexibility is high, and, after transplanting to a living body, the creation of a blood vessel and a nerve cell becomes easy and can be made to promote. Therefore, if an adipose tissue which is cultivated by such a culture apparatus is used, it is possible to restore a breast serving as a tissue body having blood and nerves equivalently to a human body. Further, such a culture apparatus can also be used for a culture of an adipose tissue of a pancreas (Langerhans' islet), and can contribute to the medical treatment of diabetes and pancreas cancer.

Figure 4:
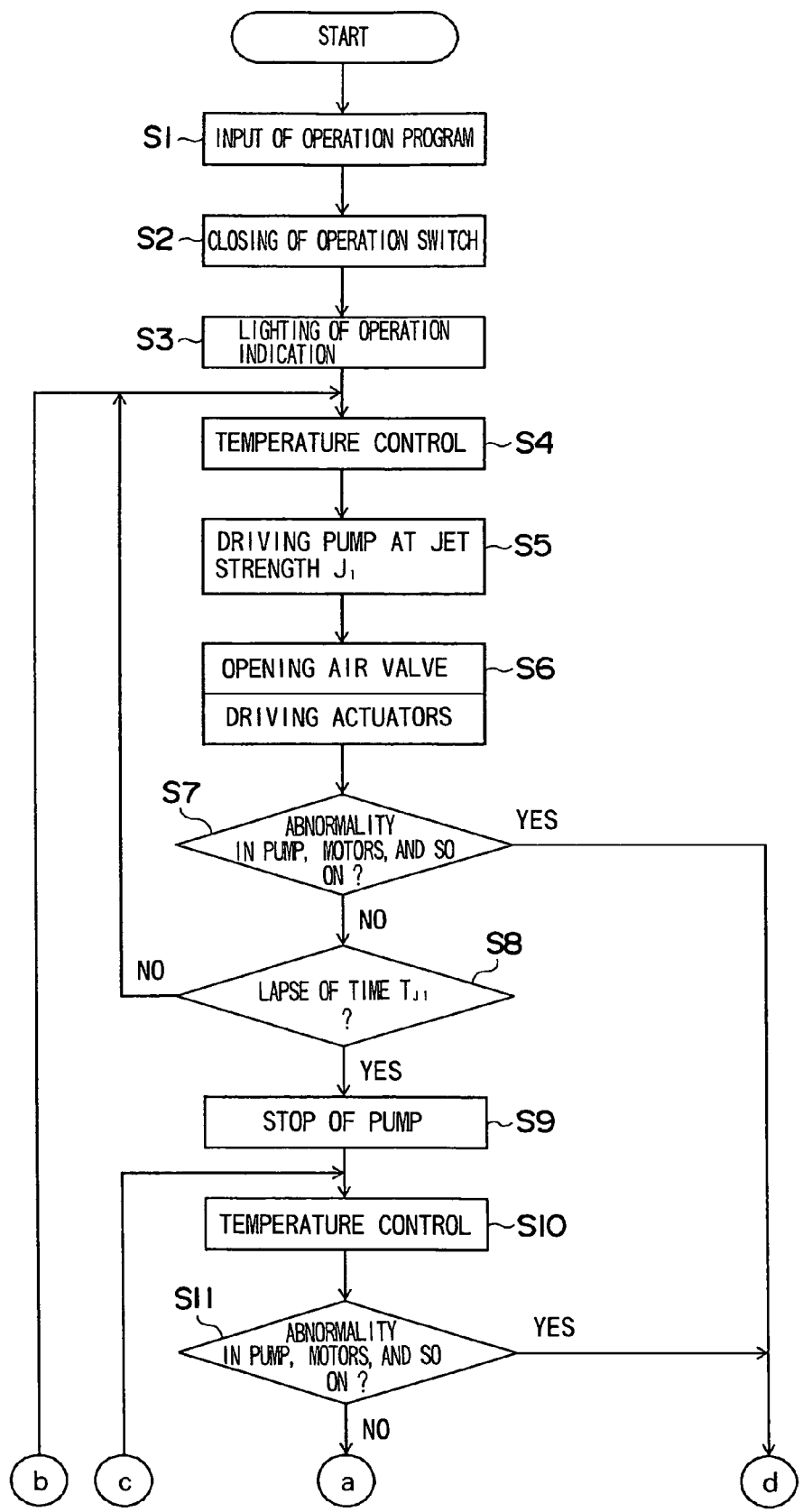
FIG. 4 is a flow chart showing a control program.
Figure 5:
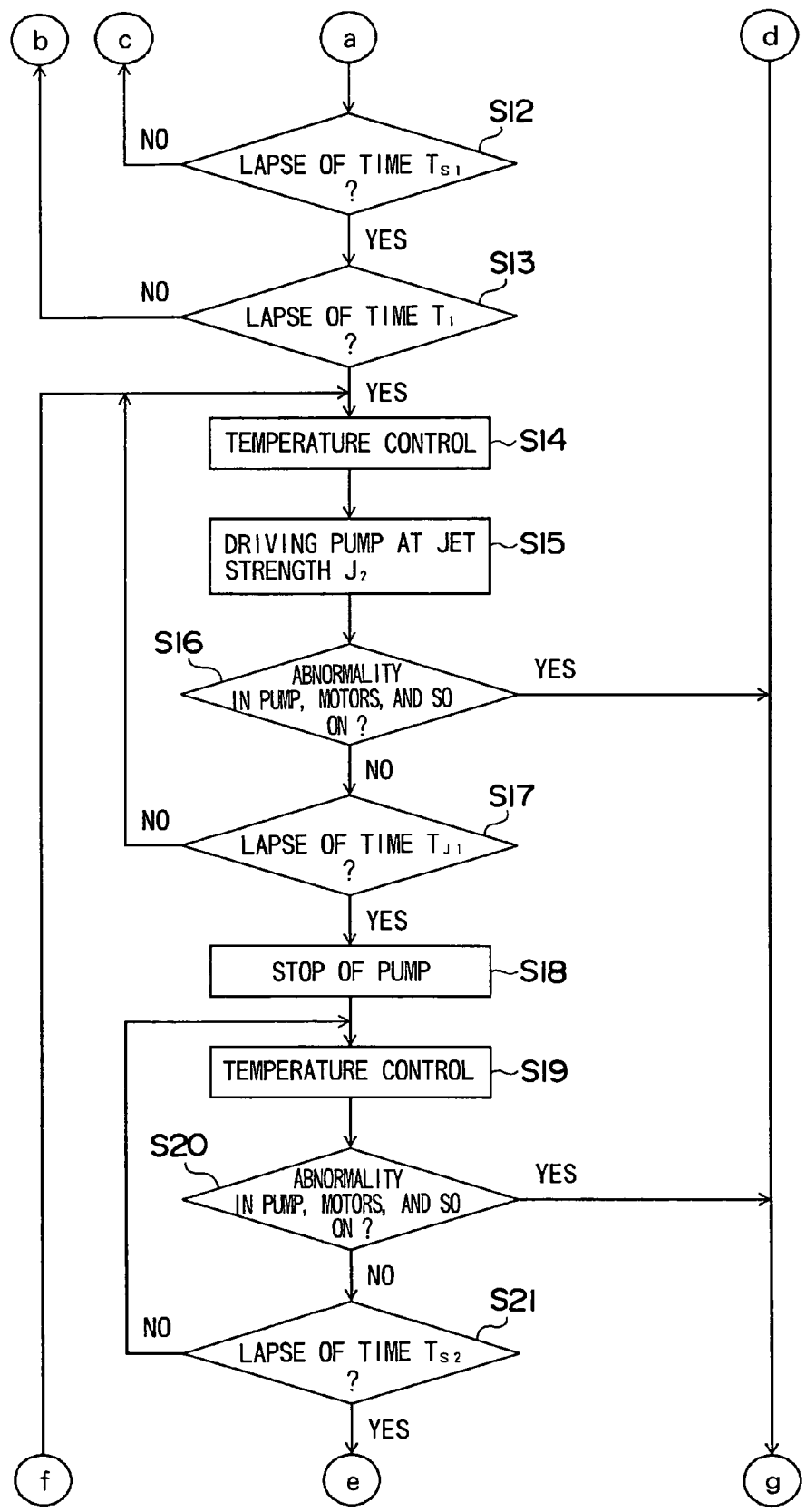
FIG. 5 is a flow chart showing a control program continued on FIG. 4.
Figure 6:
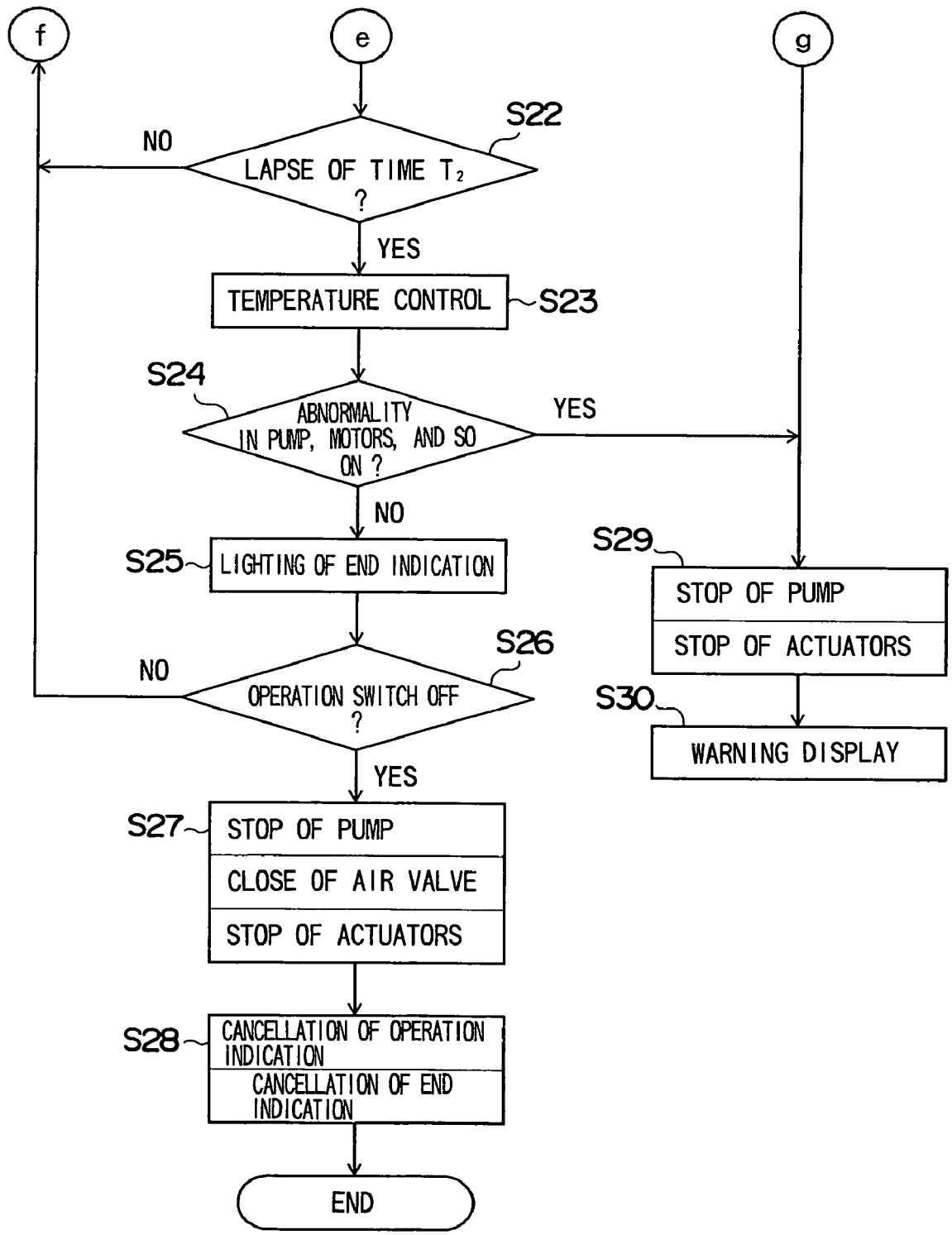
FIG. 6 is a flow chart showing a control program continued on FIG. 5.

An example of operation of a control program of this cell/tissue culture apparatus is explained by referring to flow charts in FIG. 4 through FIG. 6. In FIG. 4 through FIG. 6, reference letters "a", "b", "c", "d", "e", "f" and "g" show connectors among the flow charts.

A step S1 shows an input process of an operation program by means of the input unit 74. After a predetermined operation program is set, if the operation switch 72 is closed at a step S2, the indication lamp 76 is lighted up at a step S3, and indication representative of a state under the operation is performed. Further, at a step S4, on the basis of a comparison between a water temperature taken from the temperature sensor 68 and a set temperature, a heating temperature of the sheathed heater 66 is adjusted, and a temperature of the water 8 is controlled to a certain value.

The pump 46 is driven by the closing of the operation switch 72, and, at a step S5, the pump 46 is driven at jet strength $J_1$ consisting of low strength at the time of a start of the culture. At the following step S6, the air valve 64 is opened, and a motor of each of the actuators 54 and 56 is driven. As a result, a jet accompanied with a bubble flow is emitted in the direction of the culture chamber 18 from the nozzle 48, and a shearing stress due to the jet is given to the matrix 20 under the culture. By driving each of the actuators 54 and 56, the jet from the nozzle 48 is uniformly hit on a surface of the culture chamber 18.

Further, at a step S7, whether or not abnormality exists in the pump 46 and motors of the actuators 54 and 56 is decided. In case in which abnormality does not exist, processing proceeds to a step S8, and the operation of the pump 46 is continued by a time $T_{J1}$ (a jet time). After the lapse of the time $T_{J1}$, the processing proceeds to a step S9, and the pump 46 is stopped.

At a step S10, temperature control of the water 8 similar to the step S4 is executed, and, at a step S11, an abnormality decision similar to the step S7 is performed. In case in which abnormality does not exist, the processing proceeds to a step S12, and waiting for the lapse of a time $T_{S1}$ (a jet stop time) is performed. Then, the processing proceeds to a step S13, and waiting for the lapse of a time $T_1$ (a culture continuation time of a first stage) is performed. After that, the processing proceeds to a step S14, and temperature control similar to the step S4 is executed.

At a step S15, the pump 46 is driven at jet strength $J_2$ consisting of high strength. At a step S16, whether or not abnormality exists in the pump 46 and the motors of the actuators 54 and 56 is decided again. In case in which abnormality does not exist, the processing proceeds to a step S17, and the operation of the pump 46 is continued by a time $T_{J2}$ (a jet time). After the lapse of the time $T_{J2}$, the processing proceeds to a step S18, and the pump 46 is stopped. Then, the processing proceeds to a step S19, and temperature control similar to the step S4 is performed.

Further, at a step S20, whether or not abnormality exists in the pump 46 and the motors of the actuators 54 and 56 is decided again. In case in which abnormality does not exist, the processing proceeds to a step S21, and waiting for the lapse of a time $T_{S2}$ (a jet stop time) is performed. After the lapse of the time $T_{S2}$, the processing proceeds to a step S22, and waiting for the lapse of a time $T_2$ (a culture continuation time of a second stage) is performed. Then, the processing proceeds to a step S23, and temperature control similar to the step S4 is executed.

Further, at a step S24, whether or not abnormality exists in the pump 46 and the motors of the actuators 54 and 56 is decided again. In case in which abnormality does not exist, the processing proceeds to a step S25, and the end indication of a culture is performed at the time of a completion of the culture. Then, at a step S26, whether or not the operation switch 72 is in OFF is decided. In case of OFF, a stop of the pump 46, a close of the air valve 64 and a stop of each of the actuators 54 and 56 are performed, and, at a step S28, a cancellation of the operation indication and a cancellation of the end indication are performed.

Furthermore, in case in which a decision that abnormality exists is given at the steps S7, S11, S16, S20 and S24, the processing proceeds to a step S29, and the operation of the pump 46 and the actuators 54 and 56 is stopped. Further, at a step S30, a warning display is performed on the display unit 78 as a notification of abnormality.

Figure 7:
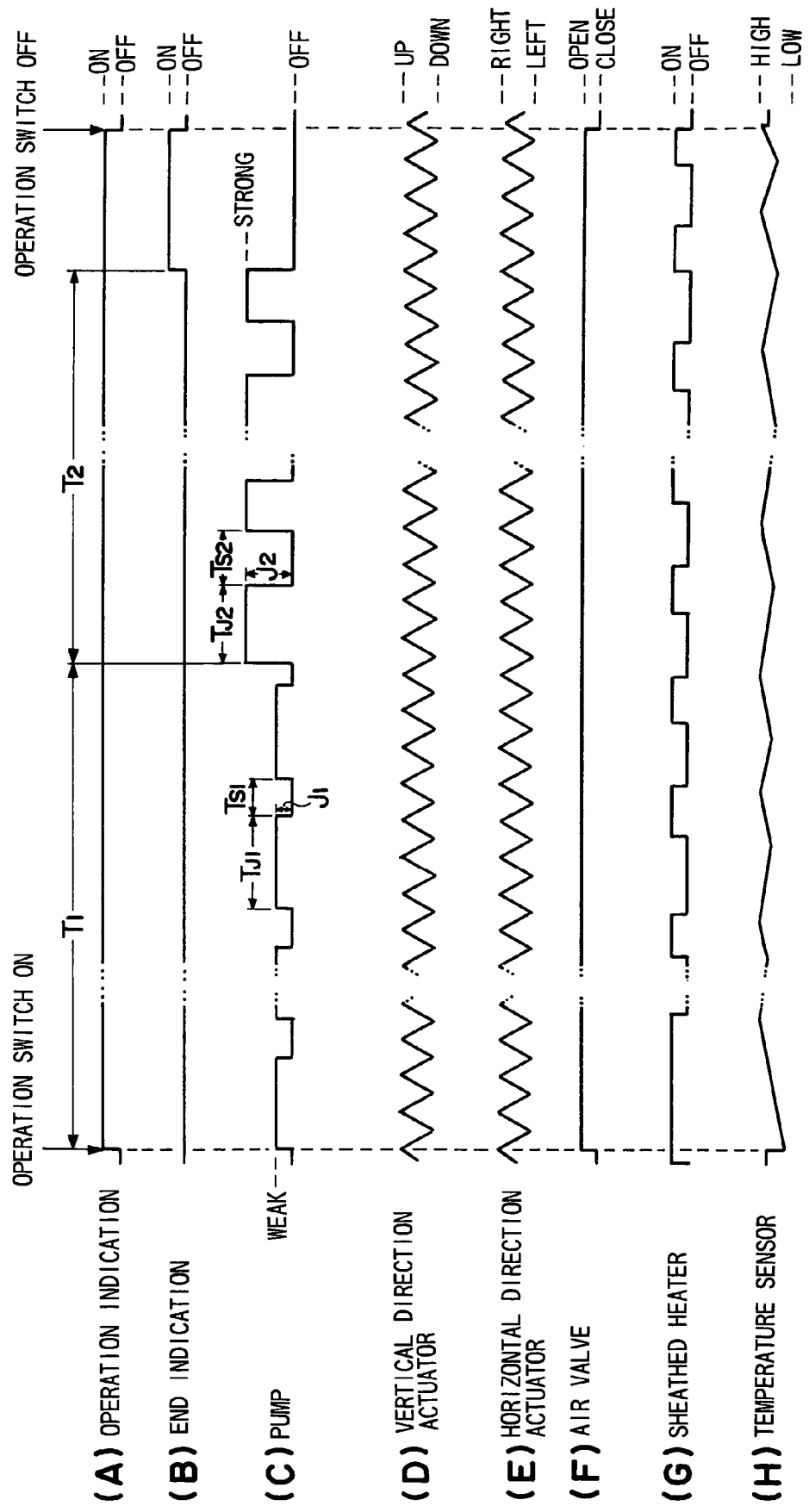
FIG. 7 is a timing chart showing a physical stimulation.

Control operation like this can be represented by a timing chart shown in FIG. 7, for example. In FIG. 7, a reference letter (A) shows the operation indication, and a reference letter (B) shows the end indication. A reference letter (C) shows the operation time and the stop time of the pump 46, and strength and weakness ($J_1$, $J_2$) of a water flow thereof. A reference letter (D) shows the movement in a vertical direction of the actuator 54, and a reference letter (E) shows the movement in a horizontal direction of the actuator 56. A reference letter (F) shows the opening and closing of the air valve 64, a reference letter (G) shows a power-supplying interval and a power-supplying stop interval of the sheathed heater 66, and a reference letter (H) shows the lapse of a detected temperature of the temperature sensor 68. As is clear from the control operation shown in FIG. 7, it is possible to vary as shown in the jet strength $J_1$, $J_2$ by an adjustment of a rotating speed of the pump 46.

Figure 8:
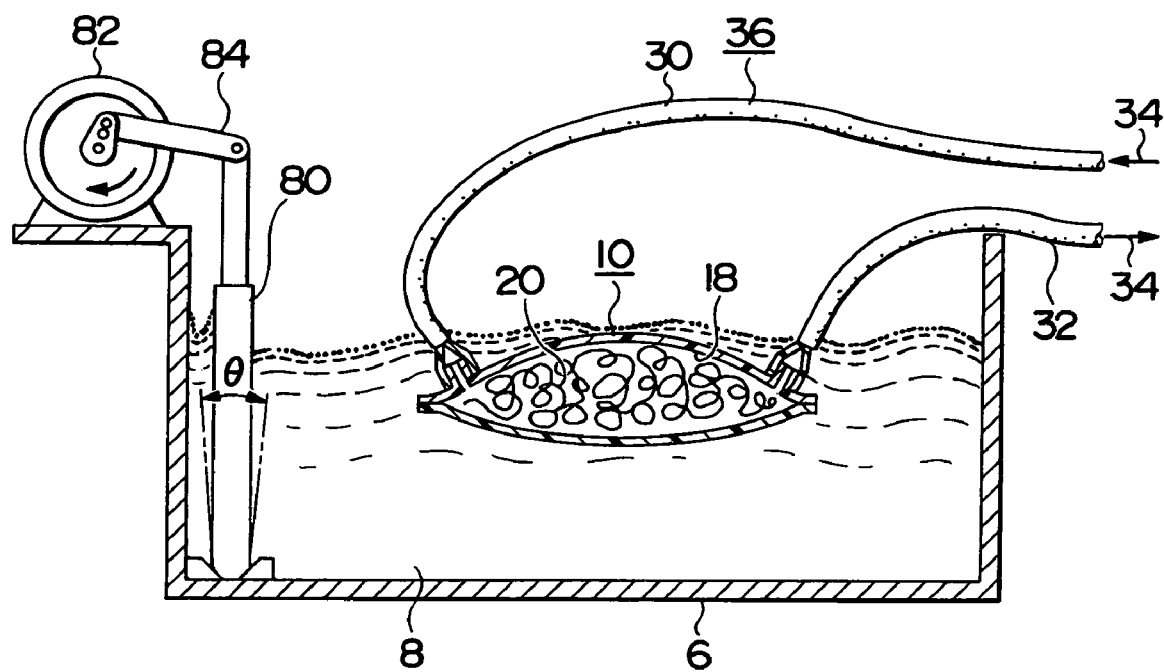
FIG. 8 is a drawing showing a second embodiment of a cell/tissue culture apparatus according to the present invention.

Next, FIG. 8 shows a second embodiment of a cell/tissue culture apparatus according to the present invention.

The cell/tissue culture apparatus of this embodiment, similarly to the first embodiment, immerses a culture vessel 10 in water 8 of a culture bath 6, and cultivates a cell or tissue on a matrix 20 in a culture chamber 18. However, this apparatus applies a shearing stress to the cell or tissue on the matrix 20 by waves serving as an oscillation of the water 8 instead of the physical stimulation by means of the jet of the water 8 in the first embodiment. Thereby, a physical stimulation is given to the cell or tissue.

In this embodiment, the culture vessel 10 namely the culture chamber 18 is provided in the water 8 of the culture bath 6 on the float. A material, a composition and a shape of the culture chamber 18, and the matrix 20 of a scaffold and so on for a culture of its inside are similar to the first embodiment. In this case, a wave generating plate 80 serving as an oscillation generating means is provided at a side wall part of the culture bath 6. To this wave generating plate 80, a rotational force which is generated by a driving means of a motor 82 and so on is converted into an angle variation θ by a link mechanism 84 and is given. Waves (standing waves) are generated in the water 8 of the inside of the culture bath 6 by means of the angle variation θ of the wave generating plate 80. As a result, it is possible to apply a physical stimulation due to the waves to the cell or tissue in the culture chamber 18.

Instead of a mechanical means of the wave generating plate 80 and the motor 82, the oscillation generating means may also be constituted so that the wave generating plate 80 is vibrated by a mechanism which converts an electric signal into a mechanical vibration, for example, by a solenoid such as a voice coil of a speaker. In this case, it is possible to generate a vibration by a frequency signal suitable for a cell or tissue.

Further, applying such a vibration to the water 8 in the culture bath 6, the culture chamber 18 is to receive various stresses of a bending stress, a shearing stress, a compressive stress and so on by the waves, and the cell or tissue on the matrix 20 of its inside receives mainly a shearing stress from various directions. Like this, the apparatus cultivates a cell or tissue while giving a physical stimulation by means of the waves.

In this case, varying the strength or frequency of the waves, for example, by a manner which controls a revolution speed or a revolution stroke of the motor 82, or by a manner which varies a current value, a frequency and/or a power-supplying interval given to the voice coil, it is possible to give a stimulation suitable for a cell or tissue to be cultivated. In addition, the strength or frequency of a physical stimulation given to a cell or tissue can be controlled according to a program which makes the strength or the frequency vary so as to make an optimum stress with the lapse of a culture time, and an effect similar to the first embodiment is obtained.

According to the cell/tissue culture apparatuses descried above, it is possible to give an optional physical stimulation of a shearing stress and so on to a cell or tissue under a culture by an oscillation of a pressure or a fluid. Further, it is possible to cultivate a tissue body according to a shape of a desired portion of a human body, and it is also possible to realize flexibility and toughness which that portion has.

The configurations, the actions and the effects as the modes for carrying out the present invention are described by referring to the embodiments shown in the drawings. However, the present invention is not limited to the modes for carrying out the present invention and the embodiments mentioned above. The present invention includes all configurations which can be predicted or conjectured by a person skilled in the art, namely, various kinds of compositions, modified examples, and so on, which are conjectured from the objects of the invention, the modes for carrying out the invention, and the embodiments of the invention.

INDUSTRIAL APPLICABILITY

As descried above, the cell/tissue culture apparatus according to the present invention gives an optimum physical stimulation of a shearing stress and so on to a cell or tissue under a culture, can be utilized for a culture of a tissue body according to a shape of a desired portion of a human body, and realizes flexibility and toughness which that portion has. Because of this, the present invention is very useful for a culture of a cell or tissue.

The invention claimed is:

1. A cell/tissue culture apparatus comprising:
a culture chamber, formed by a flexible material, that accommodates a cell or tissue to be cultivated, a culture fluid being circulated through the culture chamber by a circulation path which is attached to the culture chamber;
a culture bath in which a fluid is stored and the culture chamber is immersed in the fluid; and
a jet generation means that generates a jet in the fluid in the culture bath, makes the jet apply to the culture chamber through the fluid, and gives a physical stimulation to the cell or tissue to be cultivated in the culture chamber.

2. The cell/tissue culture apparatus of claim 1, wherein said culture chamber provides a space part of a shape according to a shape of a portion of a human body to be restored.

3. The cell/tissue culture apparatus of claim 2, wherein the cell or tissue to be cultivated is transplanted in a matrix, which is a bioabsorbable material formed like a shape of the portion of a human body to be restored, and is accommodated in the culture chamber.

4. The cell/tissue culture apparatus of claim 1, wherein said physical stimulation is a shearing stress.

5. The cell/tissue culture apparatus of claim 1, wherein said physical stimulation is given intermittently or continuously.

6. The cell/tissue culture apparatus of claim 1, wherein the jet generation means includes a structure varying direction and strength of the jet.

7. The cell/tissue culture apparatus of claim 1, wherein the jet generation means includes a means adding a bubble flow to the jet.

8. A cell/tissue culture apparatus comprising:
a culture chamber, formed by a flexible material, that accommodates a cell or tissue to be cultivated, a culture fluid being circulated through the culture chamber by a circulation path which is attached to the culture chamber, the culture chamber providing a space part of a shape according to a shape of a portion of a human body to be restored, the culture chamber being made to function as a mold for formation of the portion;
a culture bath in which a fluid is stored and the culture chamber is provided in the fluid in a floating state; and
a wave motion generating means that generates wave motion in the fluid in the culture bath, makes the wave motion apply to the culture chamber, and gives a physical stimulation to the cell or tissue to be cultivated in the culture chamber.

9. The cell/tissue culture apparatus of claim 8, wherein the cell or tissue to be cultivated is transplanted in a matrix, which is a bioabsorbable material formed like a shape of the portion of a human body to be restored, and is accommodated in the culture chamber.

* * * * *